(12) United States Patent
Guo et al.

(10) Patent No.: US 11,603,546 B2
(45) Date of Patent: Mar. 14, 2023

(54) METHOD FOR PREPARING MODIFIED STARCH AND USE THEREOF

(71) Applicant: Qilu University of Technology, Jinan (CN)

(72) Inventors: Li Guo, Jinan (CN); Hui Li, Jinan (CN); Jiahao Li, Jinan (CN); Yifan Gui, Jinan (CN); Bo Cui, Jinan (CN)

(73) Assignee: Qilu University of Technology, Jinan (CN)

( * ) Notice: Subject to any disclaimer, the term of this patent is extended or adjusted under 35 U.S.C. 154(b) by 258 days.

(21) Appl. No.: 16/934,195

(22) Filed: Jul. 21, 2020

(65) Prior Publication Data

US 2021/0222218 A1    Jul. 22, 2021

(30) Foreign Application Priority Data

Jan. 16, 2020 (CN) .......................... 202010047978.9

(51) Int. Cl.
| | | |
|---|---|---|
| *C12P 19/22* | (2006.01) | |
| *A61K 9/00* | (2006.01) | |
| *A61K 9/20* | (2006.01) | |
| *A61K 31/718* | (2006.01) | |
| *A61K 36/87* | (2006.01) | |
| *C12P 19/04* | (2006.01) | |
| *A61P 3/10* | (2006.01) | |

(52) U.S. Cl.
CPC ............ *C12P 19/22* (2013.01); *A61K 9/0056* (2013.01); *A61K 9/2013* (2013.01); *A61K 9/2059* (2013.01); *A61K 31/718* (2013.01); *A61K 36/87* (2013.01); *A61P 3/10* (2018.01); *C12P 19/04* (2013.01); *C12Y 204/01018* (2013.01); *C12Y 302/01002* (2013.01); *C12Y 302/01041* (2013.01)

(58) Field of Classification Search
CPC .... A61K 36/87; A61K 9/2027; A61K 31/718; A61K 31/012; A61K 9/0056; A61K 9/2054; A61K 9/2013; A61K 9/2059; A61P 3/10; C12Y 302/01041; C12Y 204/01018; C12Y 302/01002; C12P 19/22; C12P 19/04
See application file for complete search history.

(56) References Cited

U.S. PATENT DOCUMENTS 10,526,627 B2 * 1/2020 Skuratowicz ........... C12P 19/14

OTHER PUBLICATIONS

Guo et al., Synergistic effects of branching enzyme and transglucosidase on the modification of potato starch granules. Int. J. Biol. Mcacromol., 2019, vol. 130: 499-507. (Year: 2019).*
Li et al., Modification of rice starch using a combination of autoclaving and triple enzyme treatment: structural, physicochemical and digestibility properties. Int. J. Biol. Mcacromol., 2020, vol. 144: 500-508; published online Dec. 16, 2019. (Year: 2020).*

* cited by examiner

*Primary Examiner* — Ganapathirama Raghu

(57) ABSTRACT

Disclosed herein are methods for preparing modified starches, and uses thereof, and relates to the technical field of starch preparation; modifying a gelatinized starch suspension with β-amylase; after inactivating the β-amylase, further modifying with a branching enzyme, after inactivating the branching enzyme, further modifying with pullulanase, after inactivating the pullulanase, precipitating a resulting enzymatic hydrolysate with an alcohol to obtain precipitates; and drying the precipitates to obtain the modified starch. The methods disclosed a starch is modified remarkably, herein substantially increase the number of linear chains with a degree of polymerization DP6-11 in the starch chains and, thus, significantly increase the content of resistant starch in the modified starch—thereby facilitating the use in foods and medicaments.

3 Claims, 6 Drawing Sheets

METHOD FOR PREPARING MODIFIED STARCH AND USE THEREOF

TECHNICAL FIELD

The present invention discloses a method for preparing a modified starch and use thereof, and belongs to the technical field of starch preparation.

BACKGROUND

In recent year, the incidence of diabetes and various complications thereof increases sharply. So far, inhibiting α-glucosidase activity is a way to control hyperglycemia, and α-glucosidase inhibitors have emerged to be used in regulating postprandial hyperglycemia for therapeutic purposes. However, it has been reported that α-glucosidase inhibitors easily cause gastrointestinal diseases, such as abdominal pain, gastroenteritis, and diarrhea, in diabetic patients. Therefore, chemical inhibitors go against chronic use in diabetic patients, particularly those with poor gastrointestinal function; also, there may be other potential risk in chemical inhibitors.

Resistant starch (RS), also known as enzyme-resistant starch or indigestible starch, refers to a starch component that is indigestible in the small intestine and partly fermented in the colon to produce a large number of short-chain fatty acids; short-chain fatty acids produced thereby, such as acetic acid, propionic acid, and butyric acid, can reduce cholesterol levels and the risk of colon cancer or other cancers. In addition, RS has a low glycemic index (GI) and insulin response, and regulates body weight and blood lipid. So far, preparation methods of RS principally include acidolysis process, autoclave process, and enzymolysis process. The acidolysis process easily causes environmental pollution due to a large number of acids and bases used; the RS prepared by the autoclave process has a low yield; also, the enzymolysis process has a low yield and even lower RS content after cooking, because the method usually uses pullulanase merely to remove branched chains of the starch to obtain a limited number of linear chains with longer chain segments, followed by cooling the mutual entanglement between molecular chains to prepare RS, suggesting that the method cannot meet increasing industrial production demands.

SUMMARY

In view of the problems of the prior art, the present invention provides a method for preparing a modified starch and use thereof, substantially increasing RS content in starch and showing use of the modified starch prepared by the method of the present invention in lowering blood glucose.

A specific solution proposed by the present invention is:

a method for preparing a modified starch: β-amylase is added to the starch gelatinization solution for modification, after inactivating the enzyme, further modifying with a branching enzyme, after inactivating the enzyme, further modifying with pullulanase, after inactivating the enzyme, precipitating a resulting enzymatic hydrolysate with an alcohol to obtain precipitates, and drying the precipitates to obtain the modified starch.

In the preparation method, the gelatinized starch suspension is modified with 1000-1500 U/g dry starch weight β-amylase, after the inactivating of the enzyme, the further modifying with the branching enzyme occurs with 300-400 U/g dry starch weight of the branching enzyme, and after the inactivating of the enzyme, the further modifying with the pullulanase occurs with 10-20 U/g dry starch of the pullulanase.

In the preparation method, when the temperature is 45-55° C. and the pH of the starch paste is 5.0-5.5, β-amylase is added for modification, and the temperature after the enzyme is inactivated is 50-At 55° C., adjust the pH of the enzymatic hydrolysate to 6.0-6.5 and add branching enzyme to continue the modification. After the enzyme is inactivated, the temperature is to 50-60° C., adjust the pH of the enzymatic hydrolysate to 5.0-5.5 and add pullulanase to continue the modification.

The present invention further provides a modified starch, which is prepared by the method for preparing a modified starch.

The present invention further provides use of the modified starch in foods or medicaments.

Particularly, the present invention provides use of the modified starch in hypoglycemic foods or medicaments.

A hypoglycemic tablet includes the modified starch, grape seed procyanidins (GSPAs), a bulking agent, and a disintegrant.

The hypoglycemic tablet calculate the weight percentage, comprising 45-50 percent by weight of modified starch, 10-15 percent by weight of GSPAs, 40-45 percent by weight of bulking agent, and 10-20 percent by weight of disintegrant.

The present invention has the following beneficial effects:

The present invention provides a method for preparing a modified starch, where β-amylase, branching enzyme, and pullulanase are added to the gelatinized starch suspension successively to modify the molecular chain structure of the starch: first, α-1,4-glycosidic bonds are hydrolyzed with β-amylase to remove maltose units consecutively from non-reducing terminals of a starch chain, shorten the length of external chains of starch branches, and produces new linear chains; then, branching enzyme transfers linear chains of the starch to amylose or amylopectin through α-1,6-glycosidic bonds, forming more new branch points, i.e., new glucans with high degree of branching and short branched chain length; pullulanase hydrolyzes all the above branched chains in the starch through α-1,6-glycosidic bonds to obtain degree of polymerization (DP) 6-11 linear chains; DP 6-11 linear chains are very vulnerable to mutual entanglement of intermolecular chain segments during cryogenic cooling, significantly increasing the content of RS in the modified starch.

The present invention further provides a modified starch prepared by the above method. There are a plurality of DP 6-11 linear chains in the modified starch; these chains are very vulnerable to mutual entanglement of intermolecular chain segments to form the rearrangement and crystallization of more chains during cryogenic cooling, thereby increasing the content of RS in the modified starch significantly.

The modified starch of the present invention significantly improves taste, is more easily accepted by consumers compared with dietary fiber, can be used in foods and medicaments as main ingredient, additive, or excipient, and can be processed into the corresponding specification or shape as required.

The modified starch of the present invention is particularly suitable for use in hypoglycemic foods or medicaments. Because of high content of RS in the modified starch of the present invention, the modified starch can lower cholesterol levels, reduce GI and insulin response, and regulates body weight and blood lipid. Therefore, when used in hypoglycemic foods or medicaments, the modified starch can achieve an ideal hypoglycemic effect, and will not cause chemical inhibitor-induced adverse reactions of gastrointestinal diseases in diabetic patients.

The present invention further provides a hypoglycemic tablet, using the modified starch of the present invention and GSPAs as principal raw materials. GSPAs have an in vivo hypoglycemic effect, and play roles in reducing free radical injury and inhibiting lipid peroxidation. With hypoglycemic effects of both raw materials, the hypoglycemic tablet of the present invention improves abnormal glucose and lipid metabolism, has the same excellent hypoglycemic effect as chemical inhibitors, becomes more suitable for human consumption, and will not cause chemical inhibitor-induced adverse reactions of gastrointestinal diseases in diabetic patients. The equipment used is conventional, without the need for any special equipment; has low production cost, meets the requirements of enterprise economic efficiency, and is very suitable for industrial production.

DETAILED DESCRIPTION

Figure 1:
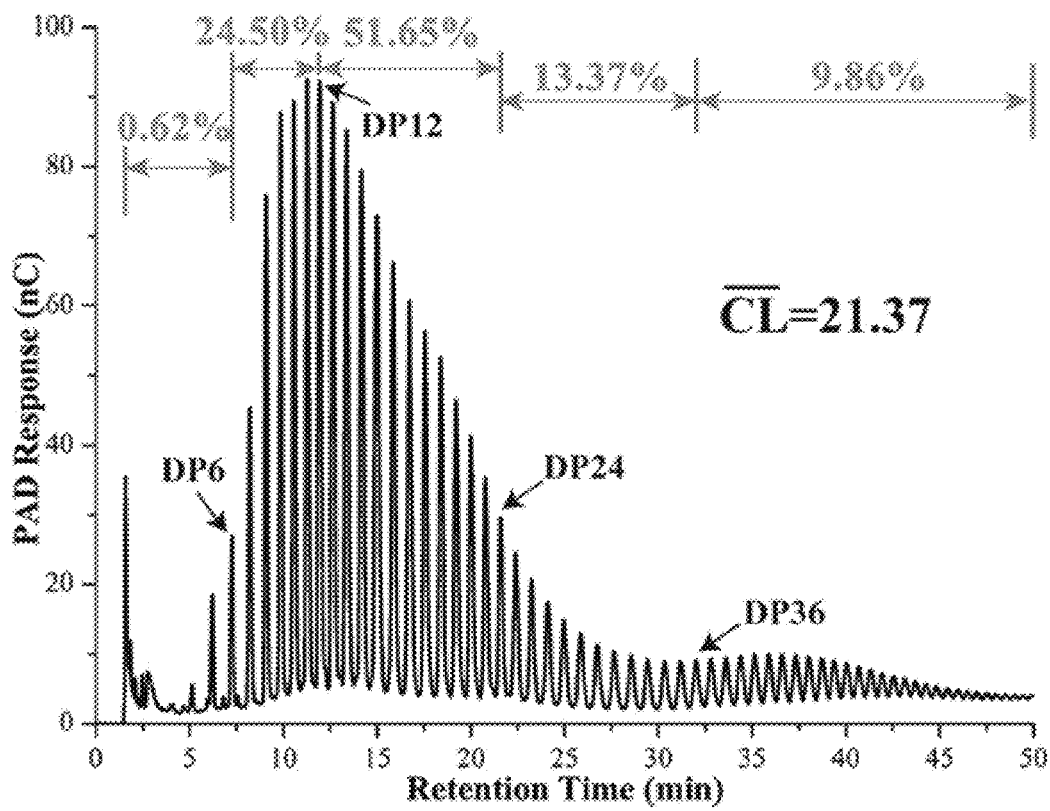
FIG. 1 shows schematically chain length distribution of original starch; DP is degree of polymerization, $\overline{CL}$ is average chain length.

The present invention will be further described in combination with accompanying drawings and specific examples so as to enable those skilled in the art to better understand and practice the invention, but the illustrated examples do not constitute any limitation to the present invention.

The present invention provides a method for preparing a modified starch: β-amylase is added to the starch gelatinization solution for modification, after inactivating the enzyme, further modifying with a branching enzyme, after inactivating the enzyme, further modifying with pullulanase, after inactivating the enzyme, precipitating a resulting enzymatic hydrolysate with an alcohol to obtain precipitates, and drying the precipitates to obtain the modified starch.

The gelatinized starch suspension may be derived from edible starch, e.g., rice starch, potato starch, Chinese yam starch, banana starch, etc. β-Amylase from barley (BA, EC 3.2.1.2), branching enzyme from *Rhodothermus obamensis* (BE, EC 2.4.1.18), and pullulanase from *Pullulanibacillus naganoensis* (PUL, EC 3.2.1.41) modify the molecular chain structure of the starch; other reagents are commercially available.

Natural rice starch has an extremely low RS content, but is frequently consumed by the Chinese. The rice starch the Chinese usually consume is taken as a specific example to describe a preparation process of the modified starch of the present invention and a process of increasing the content of RS in the modified starch:

weighing 10-20 g of rice starch, adding 100-200 mL of 0.02-0.05 mol/L sodium acetate buffer solution, adjusting to pH 5.0-5.5, stirring well, and gelatinizing in a boiling water bath for 30-35 min to obtain a fully gelatinized starch suspension.

adjusting the gelatinized starch suspension to pH 5.0-5.5, adding 1,000-1,500 U/g dry starch weight β-amylase, magnetically stirring in a water bath at 45-55° C. for 10-15 min, then heating in a boiling water bath for 20 min to inactivate the enzyme, and cooling to 50-55° C.;

adjusting the above enzymatic hydrolysate to pH 6.0-6.5, adding 300-400 U/g dry starch weight of the branching enzyme; magnetically stirring in a water bath at 50-55° C. for 10-20 min; inactivating the enzyme as described above, and cooling to 50-60° C.

adjusting the above enzymatic hydrolysate to pH 5.0-5.5, adding 10-20 U/g dry starch of the pullulanase, magnetically stirring in a water bath at 50-60° C. for 4-6 h, inactivating the enzyme as described above, and cooling to room temperature;

allowing the final enzymatic hydrolysate to stand for 20-24 h at 4-6° C., precipitating with 3-6 times the volume of absolute ethanol, and centrifuging for 10-15 min at 5,000-8,000 rpm to obtain precipitates; and drying the precipitates for 14-16 h at 40-60° C., and pulverizing to obtain modified rice starch.

In the above process, consumptions of raw materials and various reagents can be adjusted according to specific demands. For examples, in Examples 1 to 3, 10 g, 15 g. and 20 g of rice starch were weighed, respectively; accordingly, 100 mL of 0.04 mol/L sodium acetate buffer solution, 200 mL of 0.03 mol/L sodium acetate buffer solution, and 200 mL of 0.02 mol/L sodium acetate buffer solution were measured, respectively; accordingly, 1,300 U/g, 1,000 U/g, and 1,500 U/g (by dry starch weight) of β-amylase were used, respectively; accordingly, 300 U/g, 350 U/g, and 400 U/g of branching enzyme were used, respectively; accordingly, 15 U/g, 15 U/g, and 20 U/g pullulanase were used, respectively.

After detection with Starch Assay Kit, in Examples 1 to 3, the content of RS in the modified rice starch was 50.3%, 45.1%, and 56.2%, respectively; the content of RS in the cooked modified starch was 31.3%, 28.5%, and 37.7%, respectively.

Similarly, the above experimental procedure can be repeated and reproduced with the same mass of such edible starch as potato starch, sweet potato starch, and wheat starch; specifically, the content of RS in the resulting modified potato starch was 67.4-72.8%, the content of RS in the resulting modified sweet potato starch was 52.7-54.9%, and the content of RS in the resulting modified wheat starch was 60.8-66.4%.

Figure 2:
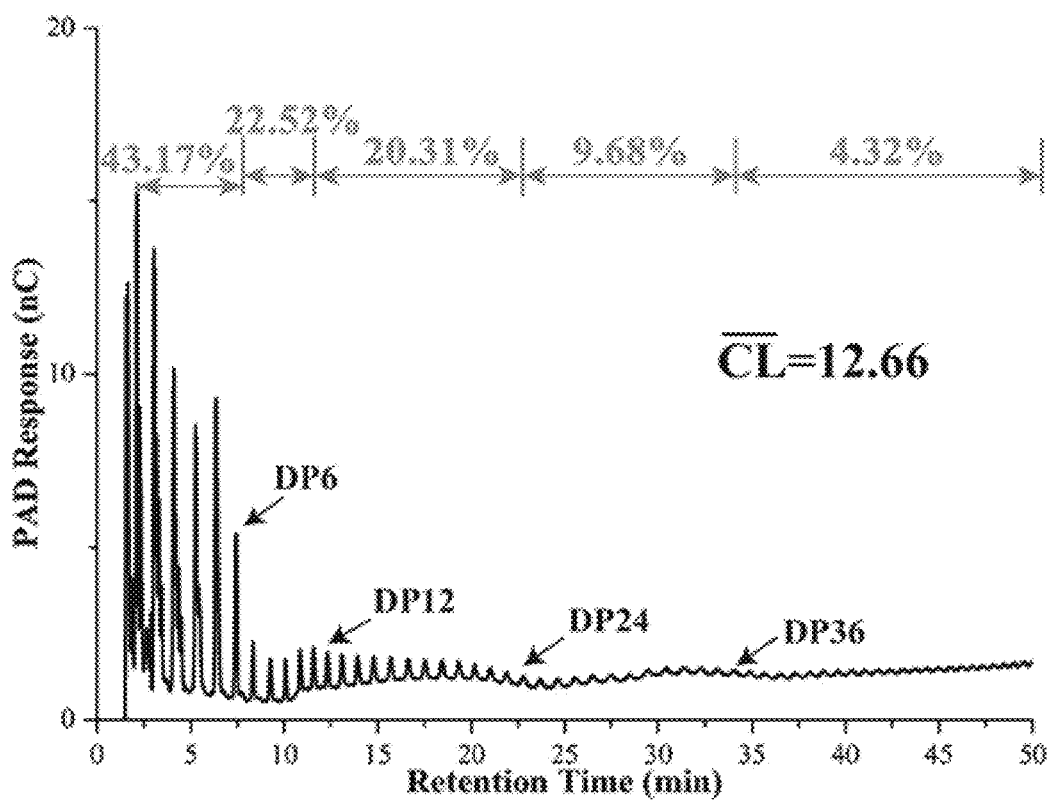
FIG. 2 shows schematically chain length distribution of the modified starch of the present invention; DP is degree of polymerization, $\overline{CL}$ is average chain length.

Specifically, chain length distribution of the modified starch was determined by high performance anion exchange chromatography with pulsed amperometric detection (HPAEC-PAD); modified rice starch sample and the corresponding native rice starch sample thereof were pretreated; 25 µL of each sample was injected into an HPAEC-PAD system and the sample was eluted at a flow rate of 1 mL/min. Two eluents were used: eluent A was 150 mM sodium hydroxide (NaOH), and eluent B was 500 mM sodium acetate in 150 mM NaOH; eluent B was mixed with eluent A for gradient elution. The resulting chain length distribution is shown in FIGS. 1 and 2. From FIGS. 1 and 2, compared with the native starch, the modified starch has more DP 6-11 short chains and fewer relatively long chains, with a significantly shorter average chain length.

The above assay was repeated with a large number of samples of the modified starch of the present invention and the corresponding native starch thereof. The resulting schematic diagram of chain length distribution indicates that, compared with the native starch, the modified starch has more DP 6-11 short chains and fewer relatively long chains, with a significantly shorter average chain length.

Figure 3:
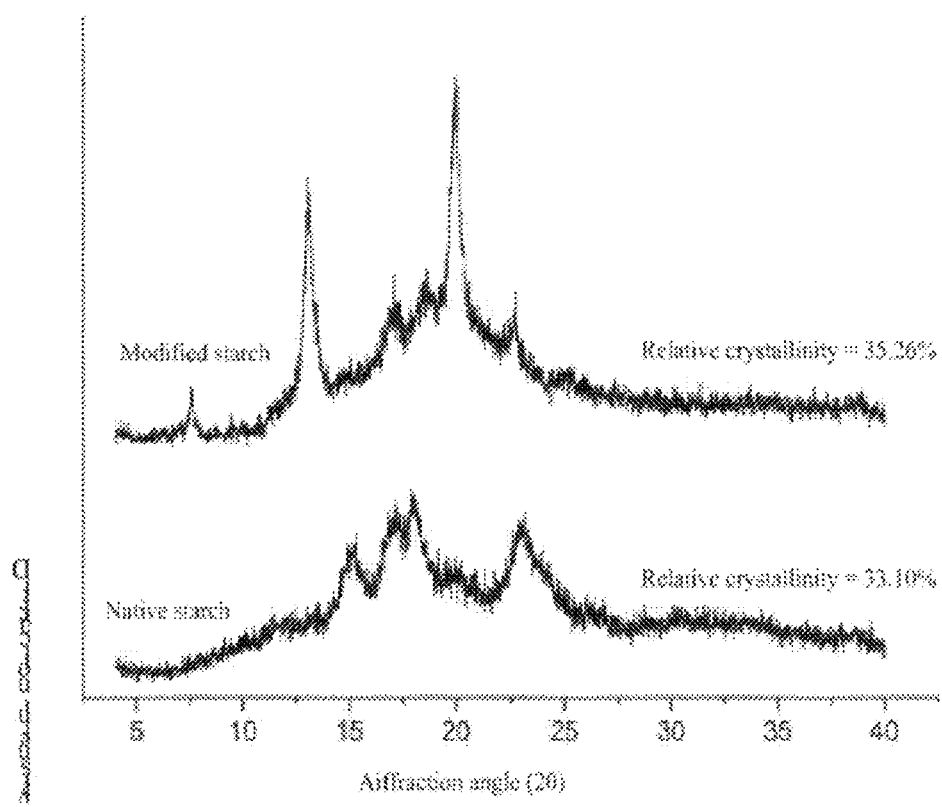
FIG. 3 shows schematically X-ray diffraction patterns and crystallinity of native rice starch and modified starch.
Figure 4:
FIG. 4 shows schematically an appearance of the hypoglycemic tablets of the present invention.
Figure 5:
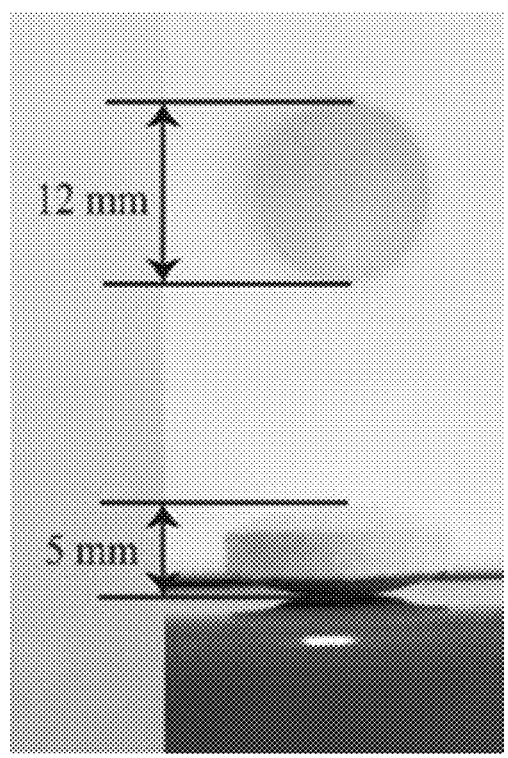
FIG. 5 shows schematically a size of the hypoglycemic tablet of the present invention.

The crystallinity of the modified starch was determined by XRD, and crystalline properties of the modified rice starch sample and the corresponding native starch were analyzed and determined by an X-ray diffractometer (XRD). The diffractometer was run at 40 kV and 40 mA, with a diffraction angle (2θ) of 5-40° and a scan rate of 10°/min. Relative crystallinity of a sample is defined as a ratio of the area of sharp crystallization peak to the total area of diffraction patterns; as shown in FIG. 3, the native starch appears an A-type crystal property, while A-type characteristic peaks of the modified starch decrease significantly and appear a V-type crystal property; compared with the crystallinity of the native starch, the crystallinity of the modified starch modified by the method of the present invention increases considerably.

The present invention further provides a modified starch prepared by the preparation process, and the digestive performance of the modified starch of the present invention and the native starch thereof is analyzed by an in vitro simulated digestion system.

In vitro digestibility and GI of the native starch and the modified starch after cooking are determined by the in vitro simulated digestion system; GI is calculated as a percentage of available carbohydrates that can be converted to glucose when hydrolyzing for 300 min. The specific process is as follows:

For example, using the rice starch and the modified starch in Example 3 as samples, each sample equivalent to 50 mg of available carbohydrates was weighed accurately in a 120 mL plastic sample cup, and the heating temperature and the rotational speed were set at 37° C. and 150 rpm, respectively.

Determination of In Vitro Digestibility:

(1) 2 mL of α-amylase from porcine pancreatic juice (250 U/mL) and carbonate buffer (pH 7) were added together to the sample cup, and the mixture was incubated for 5 min at 37° C. to simulate oral digestion;

(2) 5 mL of porcine gastric mucosa pepsin solution (1 mg/mL) and 0.02 M hydrochloric acid (pH 2) were added to the sample cup, and the mixture was incubated for 30 min at 37° C. to hydrolyze proteins;

5 mL of NaOH (0.02 M) was added to the sample cup to neutralize hydrolysate;

(3) an enzyme solution of 130 mg of pancreatin from porcine pancreas and 58.8 mg of amyloglucosidase from Aspergillus niger was dissolved in 120 mL of 0.2 M sodium acetate solution (pH 6);

25 mL of sodium acetate buffer solution (0.2 M, pH 6) and 5 mL of enzyme solution were added to each sample cup successively to simulate gut digestion. At different time intervals (20, 120, 180, 240, and 300 min), a 1 mL aliquot of hydrolysate was injected into a glucose analyzer to determine glucose concentrations, and measurements of rapidly digestible starch (RDS), slowly digestible starch (SDS), and RS in each starch sample were calculated. Results are shown in Table 1.

TABLE 1

| Sample | Nutrient component of starch | | | Glycemic index (GI) |
|---|---|---|---|---|
| | RDS (%) | SDS (%) | RS (%) | |
| Native starch | 91.5 ± 0.2 | 7.2 ± 0.2 | 1.1 ± 0.1 | 99.0 ± 0.1 |
| Modified starch | 25.2 ± 0.7 | 18.6 ± 0.4 | 56.2 ± 0.3 | 46.8 ± 0.2 |

Compared with the native starch, the modified starch prepared by the present invention significantly increases the RS content. Moreover, the modified starch significantly decreases GI compared with the native starch. The above results show that the method of the present invention significantly increase the content of RS in the modified starch; meanwhile, RS helps the modified starch of the present invention with slow digestion and absorption into bloodstream in the human body, reduces rapid hyperglycemia, and maintains glucose homeostasis in the human body; also, use of RS helps play a hypoglycemic role in hypoglycemic foods or medicaments.

The present invention further provides a hypoglycemic tablet. Using the modified starch, GSPAs, a bulking agent, and a disintegrant, the hypoglycemic tablet is manufactured through the steps of mixing raw materials and excipients, preparing the damp mass, granulating, drying, sizing the granulation, tableting, and inspecting. Specially, GSPAs and the modified starch serve as main ingredients; the bulking agent can be microcrystalline cellulose; lubricant can be magnesium stearate; the disintegrant can be crospolyvinylpyrrolidone; the bulking agent, the lubricant, and the disintegrant serve as excipients. Specific manufacturing process includes the following steps:

After passing through a 100-mesh sieve, all raw materials and excipients are mixed and dissolved in 50% ethanol solution to prepare 10-20% polyvinylpyrrolidone (PVP) solution;

45-50% modified starch, 10-15% GSPAs, and 40-45% microcrystalline cellulose are mixed well to prepare a damp mass in the presence of 10-20% PVP solution as binder; the dryness/humidity should be "compact when squeezed in the hand" by experience;

granulating: the damp mass is screened into moist granules;

the moist granules are dried at a drying temperature of 45-65° C.; the temperature rises gradually, and the granules are dried to a moisture content of 1-3%;

sizing the granulation: the dried particles are passed through a screen to screen out particles of appropriate particle size;

tableting: after sizing the granulation, 2-4% magnesium stearate is added extragranularly to the particles and mixed well; after adjusting the porch of a tablet press, the particles are filled in dies for tableting;

inspecting: the appearance, tablet weight variation, hardness, friability, disintegration time, and critical relative humidity (CRH) of tablets and GI are inspected to obtain qualified tablets.

In the above process, the specification of the hypoglycemic tablet can be customized according to the actual demands. For example, in Examples 4 to 6, the specification of the hypoglycemic tablet is specified as around 400 mg, as follows:

Example 4

Two hundred milligrams of RS, 36 mg of GSPAs, 135 mg of microcrystalline cellulose, 4 mg of magnesium stearate, and 20 mg of crospolyvinylpyrrolidone were mixed well, and prepared into a damp mass in the presence of 10% PVP solution prepared in 50% ethanol solution as binder; the dryness/humidity should be "compact when squeezed in the hand" by experience;

granulating: the damp mass was screened into moist granules;

the moist granules were dried at a drying temperature of 45° C.; the temperature rose to 60° C. gradually, and the granules were dried to a moisture content of 2%;

sizing the granulation: the dried particles were passed through a screen to screen out particles of appropriate particle size;

tableting: after sizing the granulation, 2-4% magnesium stearate vas added extragranularly to the particles and mixed well; after adjusting the punch of a tablet press, the particles were filled in dies for tableting;

inspecting: the appearance, tablet weight variation, hardness, friability, disintegration time, and CRH of tablets and GI were inspected to obtain qualified tablets.

After inspection, the functional tablet of the modified starch prepared by the present invention had a reddish brown appearance, a smooth surface, and a uniform color. The tablet was 12 mm in diameter and 5 mm in center thickness. The tablet weight variation was ±5.0%; the hardness was 53.38 IN; the disintegration time was 20.50 min; the CRH was 78.3%; and GI was 46.8.

Example 5

One hundred and fifty milligrams of RS, 30 mg of GSPAs, 150 mg of microcrystalline cellulose, 8 mg of magnesium stearate, and 25 mg of crospolyvinylpyrrolidone were mixed well, and prepared into a damp mass in the presence of 15% PVP solution prepared in 50% ethanol solution as binder; the dryness/humidity should be "compact when squeezed in the hand" by experience;

granulating: the damp mass was screened into moist granules;

the moist granules were dried at a drying temperature of 45° C.; the temperature rose to 60° C. gradually, and the granules were dried to a moisture content of 3%;

sizing the granulation: the dried particles were passed through a screen to screen out particles of appropriate particle size;

tableting: after sizing the granulation, 2-4% magnesium stearate was added extragranularly to the particles and mixed well; after adjusting the punch of a tablet press, the particles were filled in dies for tableting;

inspecting: the appearance, tablet weight variation, hardness, friability, disintegration time, and CRH of tablets and GI were inspected to obtain qualified tablets.

After inspection, the functional tablet of the modified starch prepared by the present invention had a reddish brown appearance, a smooth surface, and a uniform color. The tablet was 10 mm in diameter and 4 mm in center thickness. The tablet weight variation was ±6.0%; the hardness was 53.38 N; the disintegration time was 20.12 min; the CRH was 75.7%; and GI was 50.2.

Example 6

One hundred milligrams of RS, 30 mg of GSPAs, 100 mg of microcrystalline cellulose, 4 mg of magnesium stearate, and 20 mg of crospolyvinylpyrrolidone were mixed well, and prepared into a damp mass in the presence of 20% PVP solution prepared in 50% ethanol solution as binder; the dryness/humidity should be "compact when squeezed in the hand" by experience;

granulating: the damp mass was screened into moist granules;

the moist granules were dried at a drying temperature of 50° C.; the temperature rose to 60° C. gradually, and the granules were dried to a moisture content of 3%;

sizing the granulation: the dried particles were passed through a screen to screen out particles of appropriate particle size;

tableting: after sizing the granulation, 2-4% magnesium stearate was added extragranularly to the particles and mixed well; after adjusting the punch of a tablet press, the particles were filled in dies for tableting;

inspecting: the appearance, tablet weight variation, hardness, friability, disintegration time, and CRH of tablets and GI were inspected to obtain qualified tablets.

After inspection, the functional tablet of the modified starch prepared by the present invention had a reddish brown appearance, a smooth surface, and a uniform color. The tablet was 11 mm in diameter and 4 mm in center thickness. The tablet weight variation was ±5.5%; the hardness was 56.70 N; the disintegration was 19.83 min; the CRH was 80.6%; and GI was 56.2.

Fifty mice were pregrouped and labeled. In the experiment, type II diabetes models were established by streptozotocin (STZ) injection plus induction by high-glucose-high-fat diet. Fifty healthy male Kunming strain mice aged 4-5 weeks were selected and acclimated for one week, during which mice were observed with respect to mental status, coat color, vigor, drinking amount, urine volume, etc., and daily food intake thereof was recorded in detail, providing reference data for subsequent test substance content; the mice were grouped to receive the experiment one week after no abnormality was determined. The mice were randomized into five groups of 10 animals: normal group, diabetic control group, glimepiride group, RS group, and modified starch+GSPAs group; before modeling, the mice were weighed. Each group showed similar body weights and blood glucose levels.

The normal group was fed with normal diet for three weeks, while the remaining four groups were fed with high-glucose-high-fat diet for three weeks; then, the animals were deprived of food hut not water for 12 h; TMZ solution (which was prepared with 0.1 mol/L citric acid-sodium citrate buffer solution [pH 4.4 (4.2-4.5)] at a low temperature) was prepared when needed, and was injected intraperitoneally at a single dose of 50 mg/kg (0.5 mg/10 g) of body weight within 30 min; the mice in the normal group were given isodose citric acid-sodium citrate buffer solution and injected at a dose of 50 mg/kg every three days, during which the mice were fed with high-glucose-high-fat diet. After 72 h, the mice were deprived of food but not water for 12 h, and blood was collected from the tail vein to test the fasting blood glucose (FBG); the mice with FBG≥12 mmol/1, with obesity and polyuria were considered as the criteria for successful modeling.

Grouping and Administration by Gavage:

Ten normal and healthy mice were assigned to the normal group; the remaining successful modeled mice with type II diabetes were grouped into four groups of 10 animals according to the blood glucose level; the test period was four weeks. Specific groups are listed in Table 2: bw represents body weight.

TABLE 2

| Group No.: | Group | Feeding conditions |
|---|---|---|
| 1 | Normal | Healthy mice, basic diet, 0.4 ml of water administered by gavage |
| 2 | Diabetic control | Diabetic mice, basic diet, 0.4 ml of water administered by gavage |
| 3 | Glimepiride | Diabetic mice, basic diet, 0.4 ml (0.4 mg) of glimepiride solution administered by gavage |
| 4 | Modified starch | Diabetic mice, basic diet, 0.4 ml (21 mg) of RS solution administered by gavage |
| 5 | Modified starch + GSPAs | Diabetic mice, basic diet, 0.4 ml (21 + 3.6 mg) of RS+GSPAs solution administered by gavage |

Instructions for gavage dosing: The mice were administered by gavage once daily, in a volume of 0.4 mL.

Glimepiride group: Adults were administered 4 mg daily; the mice were administered at 1/10 of the adult dose, i.e., 0.4 mg/animal. Gavage: Glimepiride was dissolved in water to prepare a 1 mg/mL (0.4 mg/0.4 mL) solution and was administered by gavage;

Instructions for hypoglycemic tablet: tablet weighed 400 mg (including 205 mg of RS and 36 mg of GSPAs); adults were administered once daily; the mice were administered at 1/10 of the adult dose, equivalently, each animal was administered 21 mg of modified starch and 3.6 mg of GSPAs daily;

Modified starch group: 21 mg/animal. Gavage: A mixture of modified starch with water was administered;

Modified starch+GSPAs group: 21+3.6 mg/animal. Gavage: The hypoglycemic tablet was dissolved in water to prepare a solution and administered by gavage.

Figure 6:
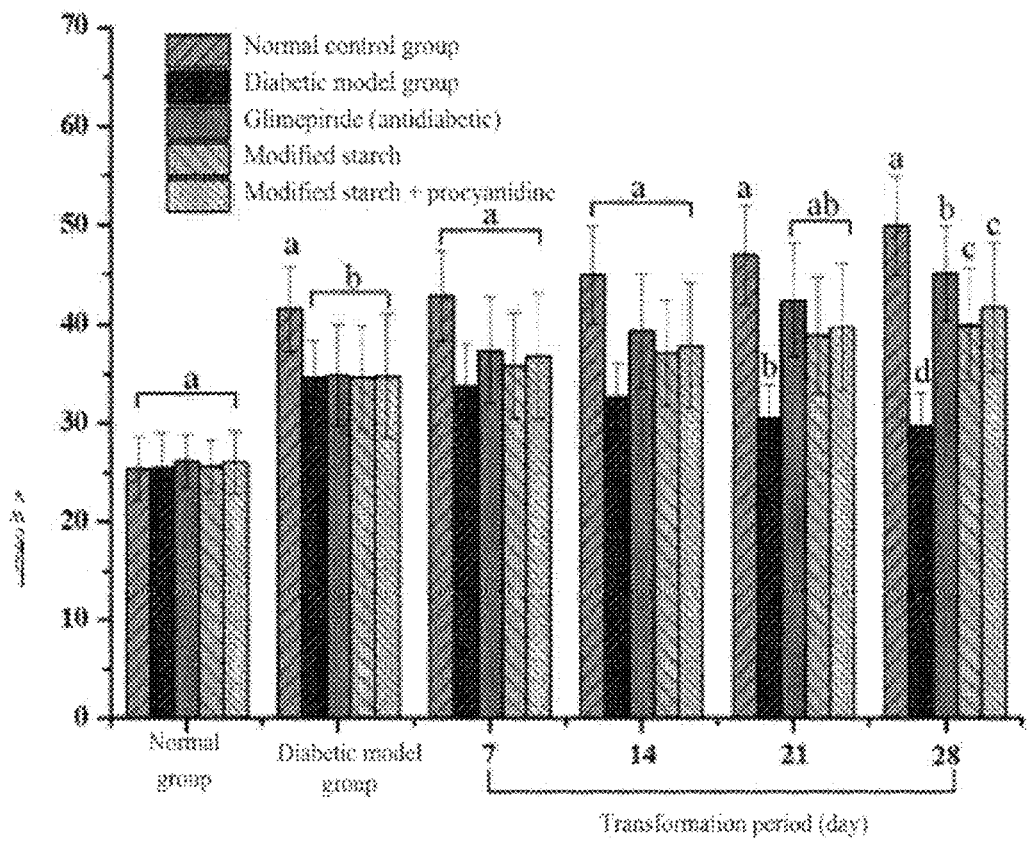
FIG. 6 shows schematically weight changes before and after mice in all pattern groups were given the hypoglycemic tablet.
Figure 7:
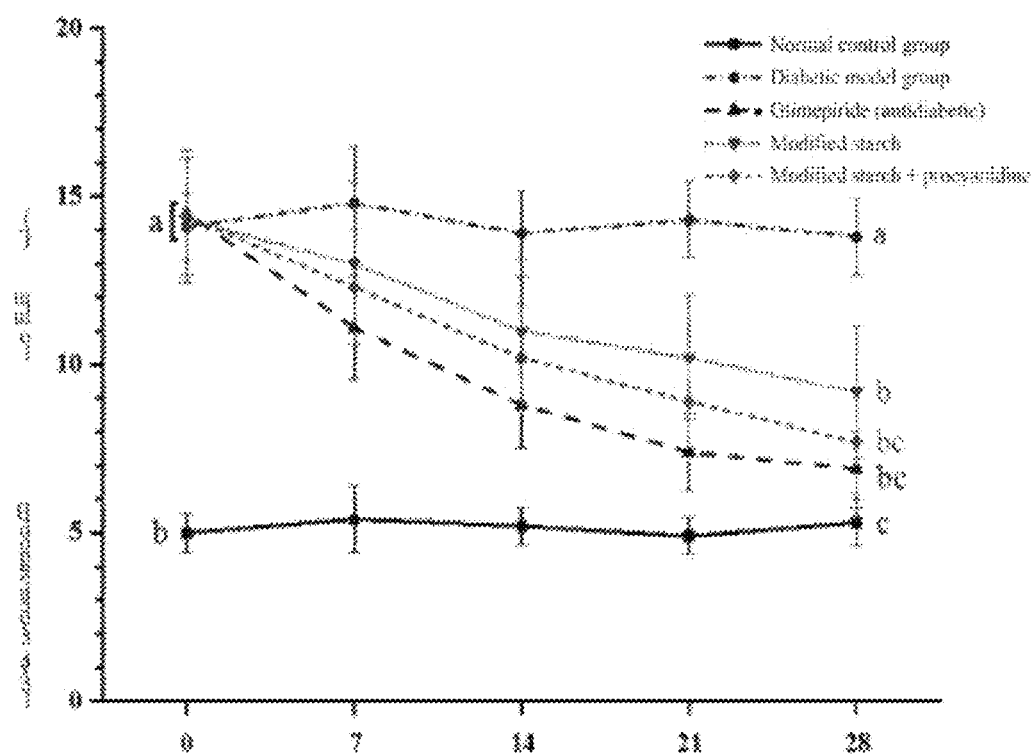
FIG. 7 shows schematically in vivo blood glucose changes before and after mice in all pattern groups were given the hypoglycemic tablet.
Figure 8:
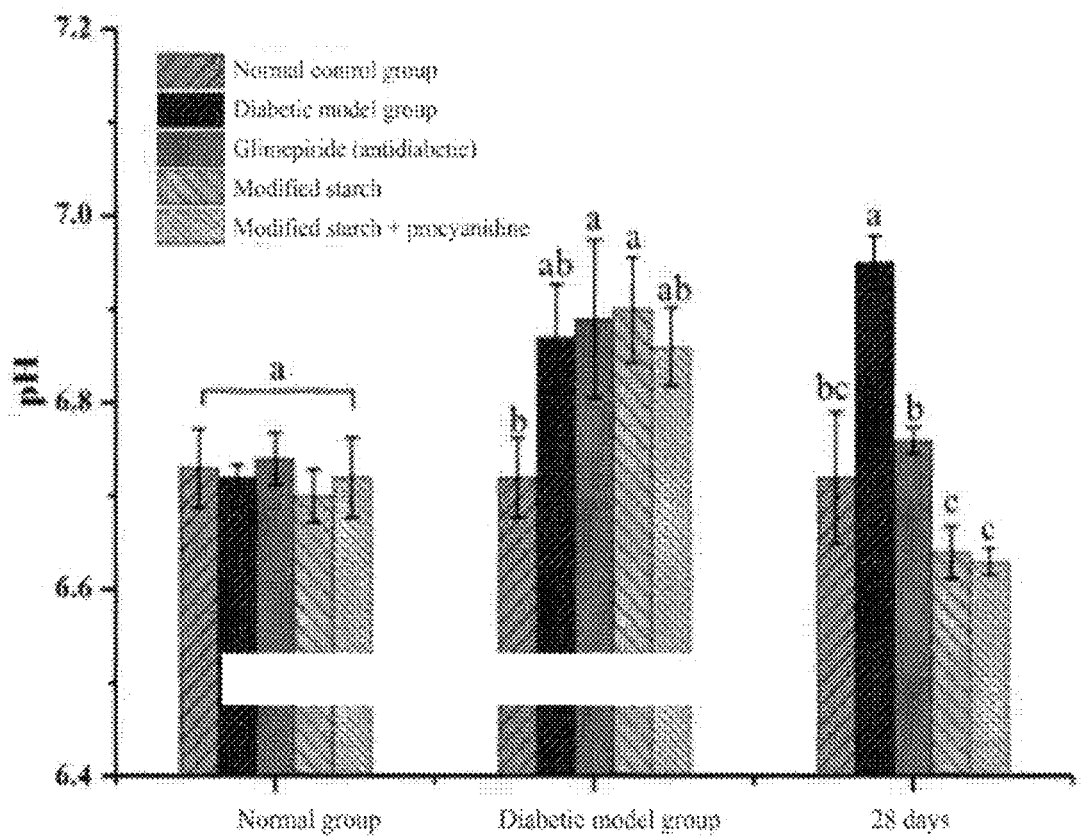
FIG. 8 shows schematically fecal pH changes before and after mice in all pattern groups were given the hypoglycemic tablet.
Figure 9:
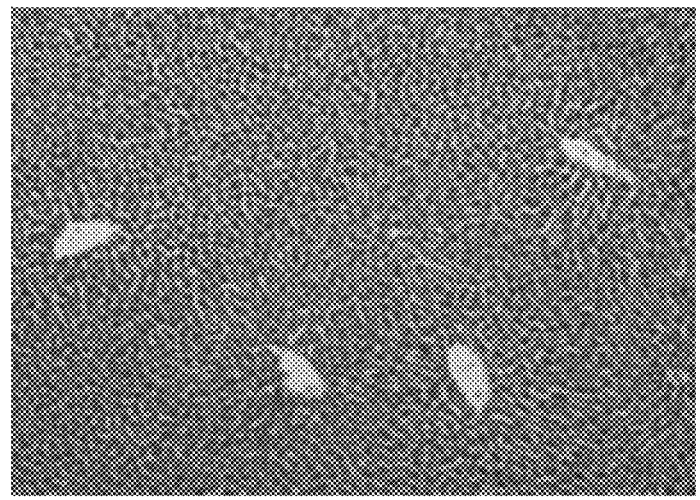
FIG. 9 shows schematically a microscopic result of hematein-eosin (HE) staining of a normal mouse liver section.
Figure 10:
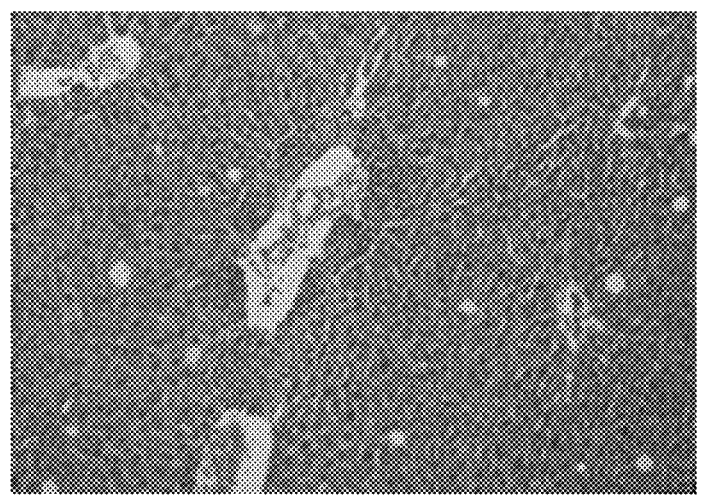
FIG. 10 shows schematically a microscopic result of HE staining of a liver section of a mouse in the diabetic model group.
Figure 11:
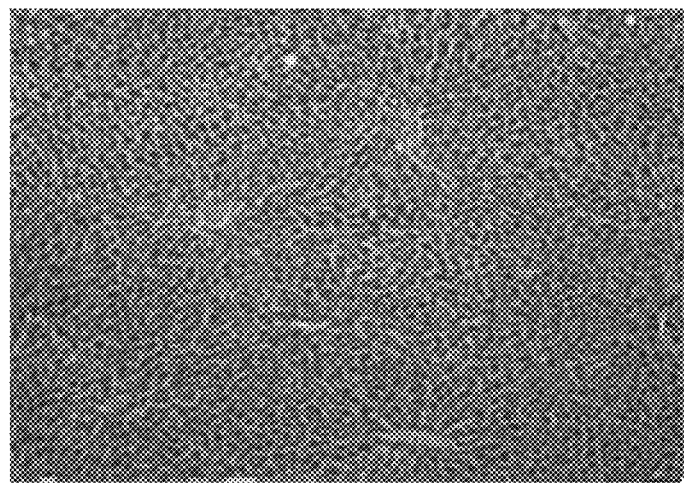
FIG. 11 shows schematically a microscopic result of HE staining of a liver section of a mouse in the glimepiride administration group.
Figure 12:
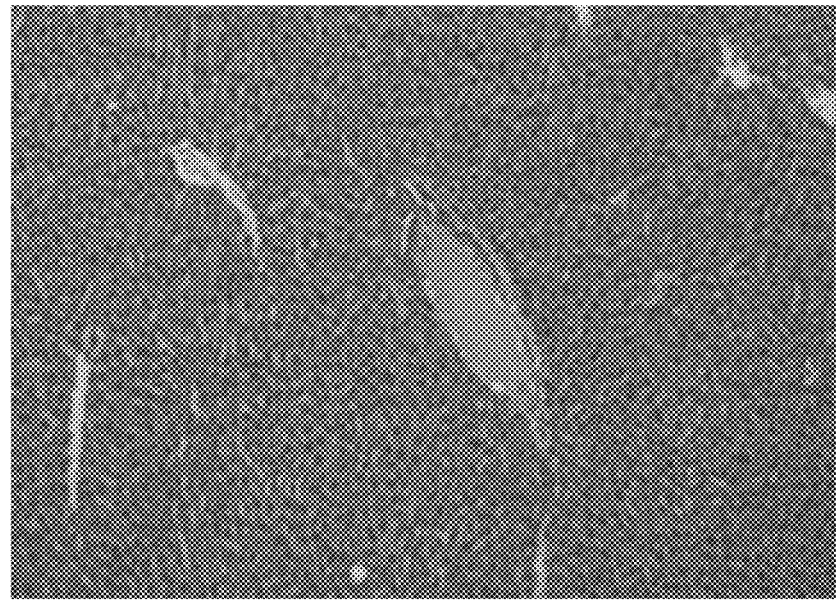
FIG. 12 shows schematically a microscopic result of HE staining of a liver section of a mouse in the modified starch administration group.
Figure 13:
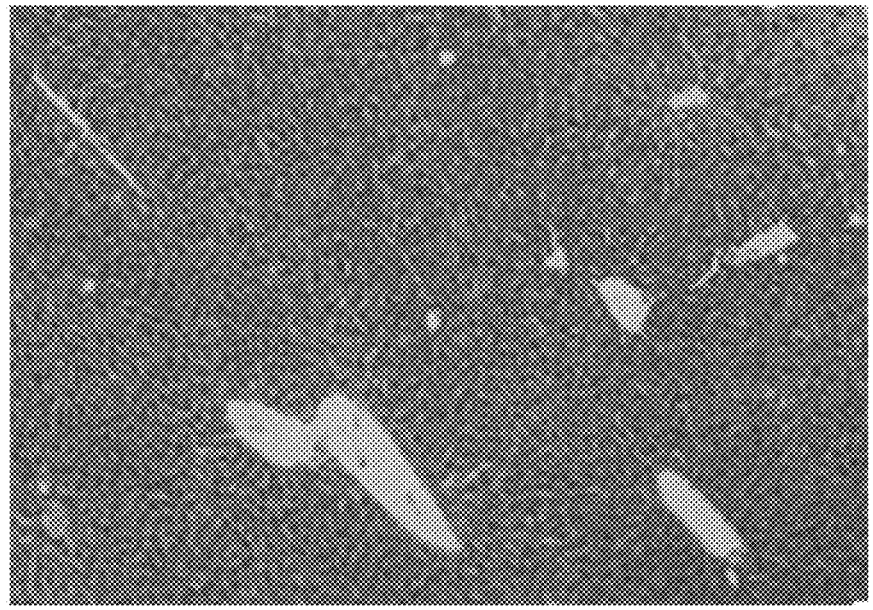
FIG. 13 shows schematically a microscopic result of HE staining of a liver section of a mouse in the hypoglycemic tablet administration group.

After 28 days, changes in weight, in vivo blood glucose, and fecal pH of mice in each model group are shown in FIGS. 6 to 8. Specifically, the modified starch and the hypoglycemic tablet provided by the present invention significantly relieve weight loss in diabetic mice synergistically, and significantly reduce hyperglycemic levels (approximately 15 mmol/L) thereof to 7-9 mmol/L. In view of mouse fecal pH, the modified starch and the hypoglycemic tablet significantly lower the fecal pH in diabetic mice of intervention groups synergistically, suggesting that main ingredients of the hypoglycemic tablet can form short-chain fatty acids beneficial to the human body in the gut and that this effect thereof is significantly superior to that of glimepiride tablet.

This indicates that the modified starch and the hypoglycemic tablet provided by the present invention play a significant role in improving diabetic symptoms and have an evident hypoglycemic effect.

Moreover, FIGS. 9 to 13 show microscopic results of HE staining of liver sections of mice in all model groups. By comparison, administration of glimepiride, modified starch, and hypoglycemic tablet in three intervention groups can improve symptoms of disordered liver cells and massive inflammatory cell infiltration in diabetic mice. Furthermore, mice have fewer inflammatory cells in the modified starch group than in the hypoglycemic tablet group, suggesting that addition of GSPAs helps inhibit inflammatory cells and improve anti-inflammatory effect.

Also, total cholesterol (TC), triglyceride (TG), and low density lipoprotein cholesterol (LDL-C) were tested for diabetic mice, as shown in Table 3.

TABLE 3

| Item | Normal control group | Diabetes model group | Glimepiride | Modified starch | Hypoglycemic tablet |
|---|---|---|---|---|---|
| TC (mmol/L) | $3.05 \pm 0.25^b$ | $5.04 \pm 0.41^a$ | $3.16 \pm 0.37^b$ | $3.85 \pm 0.47^{ab}$ | $3.36 \pm 0.43^b$ |
| TG (mmol/L) | $0.96 \pm 0.10^b$ | $1.82 \pm 0.25^a$ | $1.06 \pm 0.09^b$ | $1.33 \pm 0.16^{ab}$ | $1.19 \pm 0.12^b$ |
| High density lipid cholesterol (HDL-C)(mmol/L) | $2.48 \pm 0.36^b$ | $1.33 \pm 0.36^a$ | $2.26 \pm 0.31^a$ | $1.74 \pm 0.24^a$ | $2.07 \pm 0.26^a$ |
| LDL-C (mmol/L) | $0.50 \pm 0.06^b$ | $1.44 \pm 0.24^a$ | $0.65 \pm 0.17^b$ | $1.17 \pm 0.24^{ab}$ | $0.81 \pm 0.26^{ab}$ |

From Table 2, after intake of the modified starch and the hypoglycemic tablet by diabetic mice, IC, TG, and LDL-C decrease and HDL-C increases accordingly.

All main ingredients of the tablet provided by the present invention are natural active substances, which can improve diabetic symptoms and avoid diarrhea, abdominal distension, or other adverse reactions caused by glimepiride tablets. Therefore, the tablet is more suitable for diabetic patients.

All other reagents used in the present invention can be commercially purchased or prepared in the prior art, and the description is not repeated.

The above examples are merely preferred examples provided to more fully illustrate the present invention, and the scope of the present invention is not limited thereto. Any equivalent replacement or modification made by those skilled in the art based on the present invention should be included in the protection scope of the invention. The protection scope of the present invention is subject to the protection scope defined by the claims.

What is claimed is:

1. A method for preparing a modified starch, the method comprising:
   a) modifying a gelatinized starch suspension with β-amylase at a temperature of 45-55° C. to produce a first mixture;
   b) inactivating the β-amylase, and then modifying the first mixture with a branching enzyme at a temperature of 50-55° C. to produce a second mixture;
   c) inactivating the branching enzyme, and then modifying the second mixture with pullulanase at a temperature of 50-60° C.;
   d) inactivating the pullulanase, and then precipitating a resulting enzymatic hydrolysate with an alcohol to obtain precipitates; and
   e) drying the precipitates to obtain the modified starch.

2. The method according to claim 1, wherein:
   a concentration of the β-amylase is 1,000-1,500 U/g;
   a concentration of the branching enzyme is 300-400 U/g of the branching enzyme; and
   a concentration of the pullulanase is 10-20 U/g.

3. The method according to claim 1, wherein the gelatinized starch suspension in step a) has a pH of 5.0-5.5; the first mixture in step b) has a pH of 6.0-6.5; and the second mixture in step c) has a pH of 5.0-5.5.

* * * * *